United States Patent [19]

Tsao et al.

[11] 4,193,944

[45] Mar. 18, 1980

[54] PURGING OF INERTS IN CHLORINATED HYDROCARBON PRODUCTION

[75] Inventors: Utah Tsao, Jersey City; Angel Sy, Cedar Park, both of N.J.

[73] Assignee: The Lummus Company, Bloomfield, N.J.

[21] Appl. No.: 915,896

[22] Filed: Jun. 15, 1978

[51] Int. Cl.$^2$ ............................................. C07C 17/00
[52] U.S. Cl. ........................... 260/659 R; 260/662 R
[58] Field of Search ........... 260/659 R, 659 A, 662 R, 260/652 P; 423/481

[56] References Cited

U.S. PATENT DOCUMENTS

| | | | |
|---|---|---|---|
| 3,984,206 | 10/1976 | Winnen | 423/481 |
| 3,988,383 | 10/1976 | Huang et al. | 260/659 A |
| 3,992,460 | 11/1976 | Tsao | 260/656 R |
| 4,036,900 | 7/1977 | Strangio | 260/659 R |
| 4,039,597 | 8/1977 | Tsao | 260/659 R |
| 4,071,571 | 1/1978 | Tsao | 260/654 R |
| 4,071,572 | 1/1978 | Amato et al. | 260/659 A |
| 4,073,871 | 2/1978 | Optiz | 423/481 |
| 4,125,593 | 11/1978 | Scheifley et al. | 423/481 |

Primary Examiner—Delbert E. Gantz
Assistant Examiner—Joseph A. Boska
Attorney, Agent, or Firm—Louis E. Marn; Elliot M. Olstein

[57] ABSTRACT

A purge stream, containing inerts, some unreacted alkane and chlorinated hydrocarbon, is recovered from a chlorinated hydrocarbon production effluent and initially contacted with a first absorption oil recovered from the effluent which is at least one chlorinated hydrocarbon boiling at a temperature of at least 140° F. to absorb chlorinated hydrocarbon, followed by contacting with waste chlorinated hydrocarbon byproduct to absorb any remaining chlorinated hydrocarbon and first absorption oil. The purge gas is introduced into a combustion zone for burning waste chlorinated hydrocarbon byproduct to recover the chlorine values therefrom, and thereby utilize unreacted alkane present in the purge gas as fuel. Subsequent to recovery of the chlorine values, the inerts are purged.

10 Claims, 1 Drawing Figure

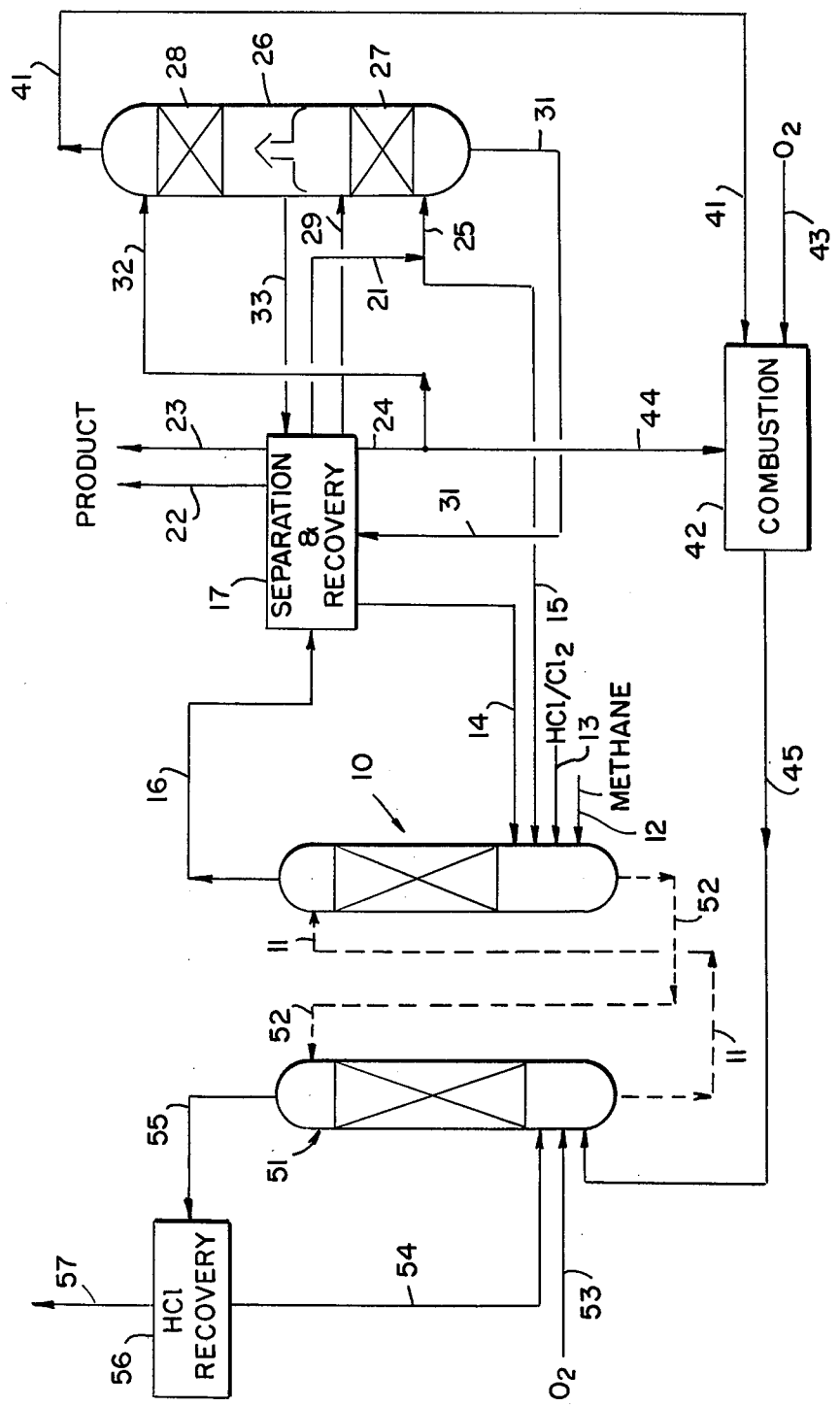

PURGING OF INERTS IN CHLORINATED HYDROCARBON PRODUCTION

This invention relates to the production of chlorinated hydrocarbons, and, more particularly to a new and improved process for purging inerts from a chlorinated hydrocarbon production system.

In the production of chlorinated hydrocarbons, such as chlorinated methanes, inerts such as nitrogen and/or carbon monoxide and/or carbon dioxide are generally present in the chlorinated hydrocarbon effluent. In order to prevent a build up of such inerts, it is necessary to purge such inerts from the system. Such inert purging systems are disclosed, for example, in U.S. Pat. Nos. 3,980,723 and 3,988,383.

The present invention is directed to an improved process for effecting purging of inerts from a chlorinated hydrocarbon production system.

In accordance with the present invention, in the production of chlorinated hydrocarbon from an alkane where there is produced a chlorinated hydrocarbon effluent containing chlorinated hydrocarbons, including waste chlorinated hydrocarbon byproducts, inerts, (nitrogen and/or carbon monoxide and/or carbon dioxide) and unreacted alkane, a purge gas stream is recovered which includes inerts, some unreacted alkane and some chlorinated hydrocarbon(s). The purge gas is initially contacted with a first absorption oil recovered from the effluent which is at least one chlorinated hydrocarbon having a boiling point of at least 140° F. to absorb chlorinated hydrocarbon present in the purge gas. The purge gas is then contacted with a second absorption oil, higher boiling than the first absorption oil, which is a portion of the waste chlorinated hydrocarbon byproduct recovered from the effluent to effect removal of any remaining chlorinated hydrocarbon originally present in the purge gas as well as any first absorption oil. The purge gas is then introduced into a waste chlorinated hydrocarbon byproduct combustion zone, along with waste chlorinated hydrocarbon byproduct recovered from the effluent and oxygen in order to effect combustion of such waste chlorinated hydrocarbon byproduct to recover the chlorine values thereof, with unreacted alkane present in the purge gas being utilized as a fuel in such combustion. After recovering such chlorine values (the chlorine values are present as the combustion products hydrogen chloride and/or chlorine), the inerts are purged from the system.

The term "waste chlorinated hydrocarbon byproduct" as used herein refers to one or more heavier chlorinated hydrocarbons produced in the chlorination which are not marketable as chlorination product and which cannot be converted in the system to marketable product. As should be apparent from the above, chlorinated hydrocarbons which are initially present in the purge gas are effectively removed therefrom, and any unreacted alkane present in the purge gas is effectively utilized for providing fuel values to the process.

The purge gas is preferably obtained from the unreacted alkane recycle stream to the chlorinated hydrocarbon production. Such recycle stream contains unreacted alkane, inerts, and some chlorinated hydrocarbon; in particular, lighter chlorinated hydrocarbons; i.e., one or more chlorinated hydrocarbons boiling below 140° F., and a portion of such recycle stream is employed as a purge gas to prevent a build up of inerts in the system.

The present invention is applicable to the production of chlorinated hydrocarbons from alkanes, most generally $C_1$ to $C_4$ alkanes, and is most particularly applicable to the production of chlorinated methanes from methane. The present invention will be further described with respect to the preferred aspect for producing chlorinated methane; however, such teachings are also applicable to the production of chlorinated hydrocarbons from, for example, ethane, propane or butane.

In accordance with the preferred aspect of the present invention, a purge gas is recovered from a chlorinated methane production effluent, containing chlorinated methanes, unreacted methane, waste chlorinated byproducts heavier than carbon tetrachloride and inerts, with the purged gas containing a portion of the inerts, a portion of the unreacted methane and a portion of the chlorinated methanes. The purge gas is initially contacted with a first absorption oil recovered from the effluent, which is chloroform, carbon tetrachloride or mixtures thereof, with such absorption oil being employed to absorb chlorinated methane present in the purge gas. The purge gas is then contacted with a portion of the chlorinated byproducts to effect further removal of chlorinated methanes, including any first absorption oil present in the purge gas. The purge gas is then introduced into a byproducts combustion zone along with chlorinated byproducts and oxygen in order to effect combustion of the chlorinated byproducts to recover the chlorine values thereof, with unreacted methane present in the purge gas being utilized as a fuel in such combustion. After recovery of such chlorine values, the inerts are purged from the system.

In this manner, chlorinated mehanes present in the purge gas are effectively recovered therefrom and any unreacted methane present in the purge gas is effectively utilized to recover the fuel and heat values thereof. The purge gas, subsequent to the second absorption step, contains some waste chlorinated byproducts; however, such chlorinated byproducts are combusted in the chlorine recovery combustion zone and, accordingly, does not result in a loss of potential valuable product.

The inerts present in the chlorinated methane effluent may be carbon monoxide and/or carbon dioxide and/or nitrogen. The carbon dioxide and/or carbon monoxide are present in the effluent as a result of oxidation of methane feed. The nitrogen may be present as a result of introduction of air, when employing a direct oxidative chlorination process, or may be present in the effluent as a result of nitrogen being employed as a carrier gas for introducing one or more components into the chlorinated methane production zone.

The purge stream may be recovered from the chlorinated methane effluent by any one of a wide variety of procedures. In general, the chlorinated methane effluent also includes water vapor, and a convenient method of separating the water vapor from the effluent is by cooling to condense water vapor therefrom, with such cooling generally resulting in the condensation of heavier chlorinated methanes and the chlorinated byproducts from the gaseous effluent, whereby a gaseous stream containing unreacted methane, inerts and some lighter chlorinated methanes; namely, methyl chloride and methylene chloride, is recovered from the cooling operation. A portion of such gaseous stream may be employed as the purge gas stream, with the remainder of such stream being recycled to the chlorinated methane production zone. In general, such a gaseous stream can be recovered by cooling the chlorinated methane effluent in one or more cooling stages, which can be indirect cooling stages or direct cooling quench cooling, to a temperature from about 40° F. to about 100° F., at pressures in the order of from about 190 psig to about 400 psig.

Although the above operation is preferred, it is to be understood that the gaseous stream containing unreacted methane inerts and chlorinated methanes can be recovered by other means; e.g., fractionation.

The chlorinated methane effluent is produced in a chlorinated methane production zone by any one of a wide variety of procedures known in the art. In particular, such chlorinated methanes are produced by an oxychlorination process in the presence of a suitable oxychlorination catalyst. In view of the fact that such procedures are generally known in the art, no details in this respect are deemed necessary for a complete understanding of the present invention.

In accordance with the preferred process, chlorinated methanes are produced by the use of a molten mixture containing the higher and lower valent chlorides of a multivalent metal, and in particular, cuprous chloride and cupric chloride, and a suitable melting point depressant, such as, potassium chloride. In accordance with such a procedure, the molten salt is oxidized in a first reaction zone, which is generally operated at a temperature of from about 700° F. to about 950° F., and preferably from 800° F. to 900° F., the operating pressure generally being in the order of from 1–10 atm. The chlorinated methane production zone is generally operated at a temperature of from 700° F. to 1200° F., preferably 700° F. to 950° F. and at operating pressures of from 1–10 atm.

The invention will be further described with respect to an embodiment thereof illustrated in the accompanying drawing, wherein:

The drawing is a simplified schematic flow diagram of an embodiment of the present invention.

Referring now to the drawing, a molten salt mixture containing a multivalent metal chloride in its higher and lower valence state, and further containing the oxychloride of the multivalent metal, as well as a suitable melting point depressant, such as a mixture of cuprous chloride, cupric chloride and copper oxychloride, with potassium chloride as a melting point depressant is introduced into a chlorinated methane production reactor, schematically indicated as 10 through line 11. The molten salt mixture is obtained as hereinafter described. Fresh feed methane in line 12, hydrogen chloride and/or chlorine in line 13, as well as recycled chlorinated methanes, if required, in line 14 and a recycle methane stream in line 15, obtained as hereinafter described, are introduced into reactor 10. Reactor 10 is operated at temperatures and pressures to effect oxychlorination of the methane, as well as conversion of recycled chlorinated methanes to desired chlorinated methane products.

A chlorinated methane production effluent is withdrawn from reactor 10 through line 16. The effluent in line 16 contains chlorinated methanes, unreacted methane and chlorinated byproducts which are heavier than carbon tetrachloride; i.e., boil higher than carbon tetrachloride, such as chlorinated dimers, as well as inerts, such as carbon monoxide and/or carbon dioxide, and nitrogen, if nitrogen is employed as a carrier gas for transportation of the molten salt. The effluent in line 16 is introduced into a separation and recovery zone, schematically generally indicated as 17. In separation and recovery zone 17, by procedures known in the art, there is recovered chlorinated methane product, recycle chlorinated methanes, chlorinated byproducts and a methane recycle stream. Thus, for example, the separation and recovery zone can include suitable means for cooling the effluent stream to condense water vapor and heavier chlorinated products therefrom and provide a remaining gas stream containing inerts, unreacted methane and some of the lighter chlorinated methanes; in particular, methyl chloride and in some cases some methylene chloride, with such stream being recovered in line 21. In addition, the separation and recovery zone may include suitable fractional distillation columns for recovering chlorinated methanes. Thus, for example, in the case where both chloroform and carbon tetrachloride are desired as chlorinated methane product, the separation and recovery zone may include a first fractional distillation column for separating components lighter than chloroform, with such components being recycled to the chlorinated methane production reactor through line 14. The bottoms from such fractional distillation column would then be introduced into a second fractional distillation column for recovery of chloroform. The bottoms from the second fractional distillation column would be introduced into a third fractional distillation column for separating carbon tetrachloride from heavier components; namely, chlorinated byproducts. The net chloroform and carbon tetrachloride products would be recovered through lines 22 and 23. The chlorinated byproducts are recovered through line 24.

A first portion of the gaseous stream in line 21 is recycled to reactor 10 through line 15. In order to prevent a build up of inerts in the system, a further portion of the stream in line 21 is recovered as a purge gas stream in line 25.

The purge gas stream in line 25, containing unreacted methane, inerts and some lighter chlorinated methanes is introduced into an absorption column 26 containing first and second absorption zones 27 and 28. The first absorption zone 27 is provided with an absorption oil through line 29, with such absorption oil being either chloroform, carbon tetrachloride or a mixture thereof, recovered from separation and recovery zone 17.

Thus, for example, the absorption oil may be conveniently a mixture of chloroform and carbon tetrachloride, recovered from a first fractional distillation column present in the separation and recovery zone 17 designed for separating components lighter than chloroform; i.e., the absorption oil is obtained from the bottoms of such absorption column. In absorption zone 27, as a result of the contact between the absorption oil and the purge gas stream, chlorinated methanes are absorbed by such absorption oil. In general, the absorption zone 27 is operated at a temperature in the order of from about 30° F. to about 120° F., and a pressure in the order of from about 15 psig to about 200 psig.

Absorption oil, containing absorbed components, is withdrawn from absorption tower 26 through line 31 and recycled to the separation and recovery zone for recovery and separation of absorbed components from the absorption oil.

Alternatively, for example, in the case where carbon tetrachloride is to be primarily recovered as product, the absorption oil may be chloroform, in which case the chloroform containing absorbed components can be recycled to the chlorinated methane production reactor for ultimate conversion to desired chlorinated methane product.

Thus, in accordance with the present invention, the absorption oil containing the absorbed chlorinated methane is recycled to at least one of the chlorinated hydrocarbon production reactor or separation and recovery zone.

The purge gas then passes into the second zone 28, and such purge gas generally contains some chlorinated methanes, and in particular a portion of the absorption oil introduced through line 29. In absorption zone 28, the purge gas is further contacted with a second absorption oil introduced through line 32. The absorption oil introduced through line 32 is a portion of the chlorinated byproducts recovered from the effluent and such absorption oil is employed to effect absorption of remaining chlorinated methanes present in the purge gas. In general, absorption zone 28 is operated at a temperature in the order of from about 50° F. to about 120° F., and a pressure in the order of from 15 psig to about 200 psig.

Absorption oil containing absorbed components is withdrawn from absorption zone 28 through line 33 and recycled to the separation and recovery zone 17 to effect recovery of absorbed components from the absorption oil.

Purge gas, which should now be essentially free of chlorinated methanes, and which still contains some unreacted methane and some of the chlorinated byproducts introduced as an absorption oil, is withdrawn from absorption zone 28 through line 41 and introduced into a combustion zone, schematically generally indicated as 42. The combustion zone 42 is provided with oxygen through line 43 and chlorinated byproducts through line 44. The combustion zone is operated to effect combustion of the chlorinated byproducts and produce a combustion effluent, containing chlorine and/or hydrogen chloride, generally both chlorine and hydrogen chloride, in addition to water vapor, carbon dioxide, carbon monoxide and nitrogen; e.g., U.S. Pat. No. 3,548,016. The combustion may be effected over a wide variety of conditions, with such combustion generally being effected at temperatures of from about 1000° F. to 3000° F., and at pressures of from about 1 to about 30 atm. Unreacted methane present in the purge gas introduced through line 41 provides fuel to maintain desired combustion conditions. In this manner, methane present in the purge gas is usefully employed to provide fuel requirements for the combustion of chlorinated byproducts. If additional fuel is required, such fuel may also be added to the combustion zone 42. In addition, if the methane present in the purge gas stream is in excess of that required for effecting combustion of chlorinated byproducts, such additional fuel generates heat, which can be effectively recovered for providing heat requirements to the overall chlorinated production system.

A combustion effluent, containing hydrogen chloride, chlorine water vapor as well as carbon dioxide and/or carbon monoxide and nitrogen, generated in the combustion, and introduced with the purge gas, is withdrawn from combustion zone 42 through line 45 and introduced into an oxidation reactor, schematically generally indicated as 51 in order to recover chlorine values therefrom.

Molten salt withdrawn from the chlorinated methane production zone 10 through line 52 is introduced into the oxidation reactor 41 wherein the molten salt is contacted with the combustion effluent introduced through line 45, molecular oxygen introduced through line 53 and recycle aqueous hydrogen chloride introduced through line 54. As a result of such contact, the molten salt is oxidized to produce copper oxychloride, and chlorine values present in the stream introduced through lines 45 and 54 are recovered by enriching the cupric chloride content of the molten salt. The molten salt, containing oxychloride, and enriched in cupric chloride is passed to the chlorinated methane production reactor 10 through line 11.

An oxidation reaction effluent is withdrawn from oxidation reactor 51 through line 55, and such effluent contains equilibrium amounts of hydrogen chloride, water vapor, nitrogen and inerts. The effluent in line 55 is introduced into a hydrogen chloride recovery zone, schematically indicated as 56, wherein aqueous hydrogen chloride is recovered for recycle to the oxidation reactor 51 through line 54. Such hydrogen chloride recovery can be effected as known in the art; e.g., as disclosed in U.S. Pat. No. 3,968,200. Chlorine present in such effluent can be converted to hydrogen chloride for recovery thereof. The remainder of the effluent is withdrawn from the hydrogen chloride recovery zone through line 57 and after neutralization of any remaining hydrogen chloride may be purged to the atmosphere. In this manner, inerts are effectively purged from the chlorinated methane production system, without loss of potentially valuable methane and chlorinated methanes.

Although the embodiment has been particularly described with respect to the production of chlorinated methanes, as hereinabove noted, the invention is also suitable in a system for the production of, for example, chlorinated $C_2$ hydrocarbons from ethane. Such a process for producing $C_2$ chlorinated hydrocarbons is described, for example, in U.S. Pat. Nos. 3,879,482 and 3,937,744.

Numerous modifications and variations of the present invention are possible in light of the above teachings and, therefore, within the scope of the appended claims, the invention may be practised otherwise than as particularly described.

We claim:

1. In a process for producing chlorinated hydrocarbons, the improvement comprising:
    (a) recovering from a chlorinated hydrocarbon production zone an effluent containing chlorinated hydrocarbon, unreacted alkane, and inerts, said chlorinated hydrocarbons including waste chlorinated hydrocarbon byproduct;
    (b) introducing the effluent into a separation and recovery zone;
    (c) recovering in the separation and recovery zone a purge gas containing a portion of the inerts, a portion of the unreacted alkane and a portion of the chlorinated hydrocarbons;
    (d) contacting the purge gas with a first absorption oil recovered from the effluent to absorb chlorinated hydrocarbon, said first absorption oil being at least one chlorinated hydrocarbon boiling at a temperature of at least 140° F.;
    (e) introducing first absorption oil, containing absorbed components into at least one of the chlorinated hydrocarbon production zone and the separation and recovery zone;
    (f) contacting purge gas from step (d) with a second absorption oil which is higher boiling than the first absorption oil, said second absorption oil being a first portion of said waste chlorinated hydrocarbon byproduct;

(g) introducing second absorption oil containing absorbed components into the separation and recovery zone to recover second absorption oil and absorbed components;

(h) introducing purge gas from step (f), oxygen and a second portion of the waste chlorinated hydrocarbon byproduct into a combustion zone to effect combustion of waste chlorinated hydrocarbon byproduct and utilize alkane present in the purge gas as fuel to thereby produce a gas containing gaseous chlorine values selected from the group consisting of chlorine, hydrogen chloride and mixtures thereof, as well as inerts; and (i) recovering the chlorine values and purging the inerts.

2. The process of claim 1 wherein a recycle gas to the chlorinated hydrocarbon production zone is recovered in the separation and recovery zone, said recycle gas containing unreacted alkane, inerts and some chlorinated hydrocarbon, and employing a portion of said recycle gas as said purge gas.

3. The process of claim 2 wherein the chlorinated hydrocarbon in the purge gas is at least one chlorinated hydrocarbon boiling below 140° F.

4. In a process for producing chlorinated methanes, the improvement comprising:

(a) recovering an effluent from a chlorinated methane production zone containing chlorinated methanes, unreacted methane, waste chlorinated hydrocarbon byproduct heavier than carbon tetrachloride and inerts;

(b) introducing the effluent into a separation and recovery zone;

(c) recovering in the separation and recovery zone a purge gas containing a portion of the inerts, a portion of the unreacted methane and a portion of the chlorinated methane;

(d) contacting the purge gas with a first absorption oil recovered from the separation and recovery zone to absorb chlorinated methanes, said absorption oil being selected from the group consisting of carbon tetrachloride, chloroform and mixtures thereof;

(e) introducing first absorption oil, containing absorbed components into at least one of the chlorinated methane production zone and the separation and recovery zone;

(f) contacting purge gas from step (d) with a second absorption oil recovered from the separation and recovery zone to absorb remaining chlorinated methanes, said second absorption oil being a first portion of said waste chlorinated hydrocarbon byproduct;

(g) introducing second absorption oil containing absorbed components into the separation and recovery zone to recover second absorption oil and absorbed components;

(h) introducing purge gas from step (f), oxygen and a second portion of the waste chlorinated hydrocarbon byproduct into a combustion zone to effect combustion of waste chlorinated hydrocarbon byproduct and utilize methane present in the purge gas as fuel to thereby produce a gas containing gaseous chlorine value selected from the group consisting of chlorine, hydrogen chloride and mixtures thereof, as well as inerts; and, (i) recovering the chlorine values and purging the inerts.

5. The process of claim 4 wherein a recycle gas to the chlorinated methane production zone is recovered in the separation and recovery zone, said recycle gas containing unreacted methane, inerts and some chlorinated hydrocarbon, and employing a portion of said recycle gas as said purge gas.

6. The process of claim 5 wherein the chlorinated methane present in the purge gas is at least one chlorinated methane boiling below 140° F.

7. The process of claim 6 wherein step (d) is effected at a temperature of from about 30° F. to about 120° F. and a pressure of from about 15 psig to about 200 psig.

8. The process of claim 7 wherein step (f) is effected at a temperature of from about 50° F. to about 120° F. and a pressure of from about 15 psig to about 200 psig.

9. The process of claim 8 wherein the recycle gas is recovered from the effluent by effecting cooling thereof to condense chlorinated methanes.

10. The process of claim 9 wherein the first absorption oil containing absorbed components is introduced into the separation and recovery zone.

* * * * *